United States Patent
Fugelsang et al.

(10) Patent No.: US 6,523,536 B2
(45) Date of Patent: Feb. 25, 2003

(54) DUAL-CANISTER INHALER HAVING A SPACER AND EASY TO OPERATE LEVER MECHANISM

(75) Inventors: Eric Fugelsang, Fishkill, NY (US); Martin Muszak, Rochester, NY (US)

(73) Assignee: Birdsong Medical Devices, Inc., Fishkill, NY (US)

(*) Notice: Subject to any disclaimer, the term of this patent is extended or adjusted under 35 U.S.C. 154(b) by 76 days.

(21) Appl. No.: 09/804,508

(22) Filed: Mar. 12, 2001

(65) Prior Publication Data
US 2002/0148462 A1 Oct. 17, 2002

(51) Int. Cl.[7] ............................................. A61M 11/00
(52) U.S. Cl. .......................... 128/200.14; 128/200.23; 128/203.15; 128/203.12; 128/203.23
(58) Field of Search ................ 128/200.23, 203.15, 128/203.12, 203.23, 200.14; 239/338, 305; 22/145.1, 144.5, 135

(56) References Cited

U.S. PATENT DOCUMENTS

| | | | | |
|---|---|---|---|---|
| 3,704,725 A | * | 12/1972 | Marand | 137/550 |
| 4,083,368 A | * | 4/1978 | Freezer | 128/203.22 |
| 4,470,412 A | | 9/1984 | Nowacki et al. | |
| 4,790,305 A | | 12/1988 | Zoltan et al. | |
| 4,791,149 A | * | 12/1988 | Pocknell | 206/221 |
| 4,809,692 A | | 3/1989 | Nowacki et al. | |
| 4,832,015 A | | 5/1989 | Nowacki et al. | |
| 4,926,852 A | | 5/1990 | Zoltan et al. | |
| 5,002,048 A | * | 3/1991 | Makiej | 128/200.23 |
| 5,007,419 A | * | 4/1991 | Weinstein et al. | 128/200.14 |
| 5,012,803 A | | 5/1991 | Foley et al. | |
| 5,012,804 A | | 5/1991 | Foley et al. | |
| 5,040,527 A | | 8/1991 | Larson et al. | |
| 5,042,467 A | | 8/1991 | Foley | |
| 5,385,140 A | | 1/1995 | Smith | |
| 5,427,089 A | | 6/1995 | Kraemer | |
| 5,437,267 A | * | 8/1995 | Weinstein et al. | 128/200.23 |
| 5,645,049 A | | 7/1997 | Foley et al. | |
| 5,664,557 A | * | 9/1997 | Makiej, Jr. | 128/200.23 |
| 5,816,240 A | | 10/1998 | Komesaroff | |
| 5,848,588 A | | 12/1998 | Foley et al. | |
| 5,988,160 A | | 11/1999 | Foley et al. | |
| 6,026,807 A | | 2/2000 | Puderbaugh et al. | |
| 6,071,498 A | | 6/2000 | Narodylo et al. | |
| 6,125,844 A | | 10/2000 | Samiotes | |

OTHER PUBLICATIONS

WE Pharmaceuticals, Inc., E–Z Spacer™ & E–Z Spacer Mask (SMALL), http://www.weez.com.

Demirkan et al., "Salmeterol administration by metered–dose inhaler alone vs. metered–dose inhaler plus valved holding chamber," *Chest*, v.117 (2000) pp. 1314–1318.

Finlay and Zuberbuhler, "In vitro comparison of beclomethasone and salbutamol metered–dose inhaler aersols inhaled during pediatric tidal brething from four valved holding chambers," *Chest*, v.114 (1988) pp. 1676–1680.

(List continued on next page.)

*Primary Examiner*—Glenn K. Dawson
*Assistant Examiner*—Darwin P. Erezo
(74) *Attorney, Agent, or Firm*—Kenyon & Kenyon (57) ABSTRACT

The present invention relates to a dual-cannister inhaler for effectively delivering medications by inhalation through the mouth of patients, having a spacer for more effectively mixing the medication and air, and easy to operate lever and canister selection mechanisms. A preferred embodiment of the invention has universal receptors for two metered dose inhaler canisters. A lever arm is provided that is opposed to the body of the inhaler, which allows a patient to use the entire hand to activate the metered dose inhaler canister. A simple and easy to operate sliding selector permits one-handed control of the canister selector. In a preferred embodiment a valve assembly and whistle are included in the inhaler to improve the consistency and effectiveness of delivery of medication to the lungs of a patient.

14 Claims, 8 Drawing Sheets

OTHER PUBLICATIONS

Konig, "Spacer devices used with metered–dose inhalers. Breakthrough or gimmick!" *Chest*, v.88 (1985) pp. 276–284.

"New Methods May Mean Fewer Insulin Shots for Diabetic, Inhalers and Pills Are Among Advances Now Being Tested", http: www.msnbc.com neWS 525058.asp. May 30, 2000.

* cited by examiner

DUAL-CANISTER INHALER HAVING A SPACER AND EASY TO OPERATE LEVER MECHANISM

FIELD OF THE INVENTION

The present invention relates to a dual-cannister inhaler for effectively delivering medications by inhalation through the mouth of patients having a spacer for more effectively mixing the medication and air, and an easy to operate lever mechanism.

BACKGROUND OF THE INVENTION

Inhalation into the lungs of a patient of a metered dose of medication is an increasingly common delivery system for a variety of drugs, including but not limited in any way to anti-asthma medications, insulin (See http.// www.msnbc.com/news/52508.asp), various steroids and treatments specific to various pulmonary diseases. One concern with metered dose inhalers or aerosol pressurized cartridges has been that, while the metered dose inhaler canister dispenses a fixed, metered dose of medication, not all of the metered dose actually reaches the lungs of the patient. Even if a patient times inhalation with the dispersal of the medication from the metered dose inhaler (MDI), the amount of medication reaching the lungs is inconsistent, depending on how much of the medication is dissolved and entrained in the stream of air entering the patient's lungs, and how much of the medication is deposited on surfaces of the inhalation apparatus, the mouth and oropharyngeal area of the patient. Furthermore, deposits in the mouth and oropharyngeal area of the patient can cause complications, such as candidiasis, as well as leave an unpleasant aftertaste. In addition, many patients using inhalation devices have practical problems with the use of typical inhalers, including difficulty with compressing the metered dose inhaler canister, problems timing inhalation with the dispersal of medication, and inability to inhale the complete dose of medication in a single breath, particularly young, elderly, or patients who suffer from asthma and dysphonia or thrush from inhaled corticosteroids. In practice, it is common to see patients activating their metered dose inhalers multiple times, although the metered dose should have been dispensed in a single activation. This is a typical response of patients to the difficulty and inconsistency of medication delivery, undermining the effectiveness of the MDI, which can lead to over-medication, under-medication, or waste and higher than necessary costs for treatment.

The typical solution to the problem of inconsistent medication delivery has been to provide a "spacer" or "chamber" within the inhalation device. A spacer or chamber is merely a reservoir of air. The metered dose of medication, usually an atomized mist or vapor, mixes with the reservoir of air before being inhaled by the patient, reducing the inconsistency of delivery due to timing difficulties. See U.S. Pat. Nos. 4,470,412; 4,790,305; 4,926,852; 5,012,803; 5,040,527; 5,042,467; 5,816,240; and 6,026,807. An additional improvement incorporated into many of the devices with spacers has been a simple valve mechanism to allow the patient to inhale the medication in more than one breath. For example, see U.S. Pat. Nos. 4,470,412; 5,385,140. The efficacy of such devices for correcting errors in patient technique has been shown in general medical research. For example, see Demirkan, et al., "Salmeterol Administration by Metered-Dose Inhaler Alone vs. Metered-Dose Inhaler Plus Valved Holding Chamber," *Chest* 117 (2000) pp. 1314–1318, Finlay and Zuberbuhler, "In vitro comparison of beclomethasone and salbutamol metered-dose inhaler aerosols inhaled during pediatric tidal breathing from four valved holding chambers," *Chest* 114 (1998) pp. 1676–1680, and Konig, "Spacer devices used with metered-dose inhalers. Breakthrough or gimmick?" *Chest* 88 (1985) pp. 276–284.

One problem not generally addressed is the ease of compression of MDI canisters. One spacer, called the EZ Spacer®, http://www.weez.com, improves the ease of compression by allowing the patient or another to use both thumbs on a pull handle and the forefingers on the MDI canister, but this is only a marginal improvement over the standard design, allowing merely one thumb and forefinger for compression of the MDI, and is no aid to patients who do not have full use of both of their thumbs and forefingers.

For infants or other patients who have difficulty using a mouthpiece, a mask is commonly attached or incorporated onto the MDI inhaler. See U.S. Pat. Nos. 4,809,692; 4,832,015; 5,012,804; 5,427,089; 5,645,049; 5,988,160. Also, some devices include an audible signaling device to warn patients when inhalation exceeds a desirable rate. For example, see U.S. Pat. Nos. 4,809,692 and 5,042,467.

One method of attaching a spacer to the MDI cannister is to insert the MDI inhaler into a universal adapter such as shown in U.S. Pat. No. 5,848,588, but this is bulky and awkward to use, and does nothing to ease the difficulty of compressing the MDI canister for infirm or ailing patients. Other devices are designed to have a specific MDI canister inserted into the device. It would be beneficial to be able to insert MDI canisters for various medications into an inhaler with a universal receptor.

SUMMARY OF THE INVENTION

The present invention is directed to an inhaler that has universal receptors for multiple medication canisters 10, 11 or metered dose inhaler (MDI) canisters, also referred to as cartridges. One typical embodiment of the invention accepts two canisters (dual canisters), and has a lever arm 22 that is easy to depress, a chamber 24 that acts as a spacer, and a mouthpiece 25, having an optional valve mechanism 62 and over-pressure whistle 63, that improves the efficiency of medication delivery, and a slidable selector switch 21 that permits the user to select the mode of operation. The modes of operation include selecting either of the two canisters individually. An additional non-operational setting locks the actuator lever 23 to prevent inadvertent dispensing of medication during periods of non-use.

One object of the invention benefits patients who are infirm or young, by reducing the difficulty in using an inhalation device. The actuator lever 23 allows the entire hand to be used in depressing the MDI canister, and also provides a mechanical advantage, reducing the pressure necessary to dispense the medication. The sliding selector switch 21 is easy to manipulate, and can be put into position to operate either of the dual canisters individually with one hand. The optional locking position can also be selected by a patient with only one hand. An optional indicator shows which of the two canisters is selected by the sliding selector switch.

In a preferred embodiment of the multi-canister inhaler, the dual canister design allows two different kinds of medication to be dispensed by a single inhaler. Increasingly, patients require multiple MDI medications, and the use of a single inhaler for two different medications, which reside conveniently within the inhaler, reduces problems with storage, retrieval, and insertion of MDI canisters into the inhaler for those that are infirm, young or in distress. Alternatively, the second canister may be inserted as a reserve supply for those patients that require assistance with insertion of canisters into an inhalation device, allowing the patient to switch to the reserve supply by merely pushing the sliding selector switch.

In one embodiment, the standard, universal cowling is designed to accept MDI canisters of nearly all commonly prescribed medications, and the cowling helps to guide the canister into the inlet port of the housing when the patient inserts a MDI canister into the inhaler. In addition, the cowling provides support to the canister when the patient depresses the actuator lever, dispensing medication into the housing of the inhaler. Specialized cowlings may be designed for unusual MDI canisters or new MDI canisters that would not fit the universal cowling. By universal, the inventors mean that the cowling is designed to accept nearly all commonly prescribed MDI canisters.

Upon dispensing the medication, the atomized mist from the inhaler is directed through the housing and into the chamber. During inhalation by the patient, a vent in the housing brings fresh air into the housing sweeping the remaining atomized mist from the housing into the chamber, where it mixes with the air, and is drawn into the patients lungs through the patients mouth. In one preferred embodiment of the invention a valve assembly in the mouthpiece of the chamber allows the mixture of medication and air to be drawn through the mouthpiece during inhalation, see FIG. 8, for example, but during exhalation, the inhalation valve closes, and an exhalation valve opens, allowing the exhaled air to escape from an exhalation vent in the mouthpiece. This allows the patient to inhale the medication in multiple breaths.

It should be obvious to one of ordinary skill in the art that an inhaler with access ports for more than two canisters could be configured in the same way as the dual canister design shown in the figures, and presented in the detailed description of the invention. Indeed, the invention is not limited to a dual canister design, but would include a multiple canister design, which includes a sliding selector switch able to engage each of the multiple MDI canisters inserted into an expanded cowling.

BRIEF DESCRIPTION OF THE FIGURES

For the purpose of illustrating the invention, representative embodiments are shown in the accompanying figures, it being understood that the invention is not intended to be limited to the precise arrangements and instrumentalities shown.

DETAILED DESCRIPTION OF THE PREFERRED EMBODIMENTS

The present invention will now be described in detail for specific preferred embodiments of the invention. These embodiments are intended only as illustrative examples and the invention is not to be limited thereto.

Figure 5:
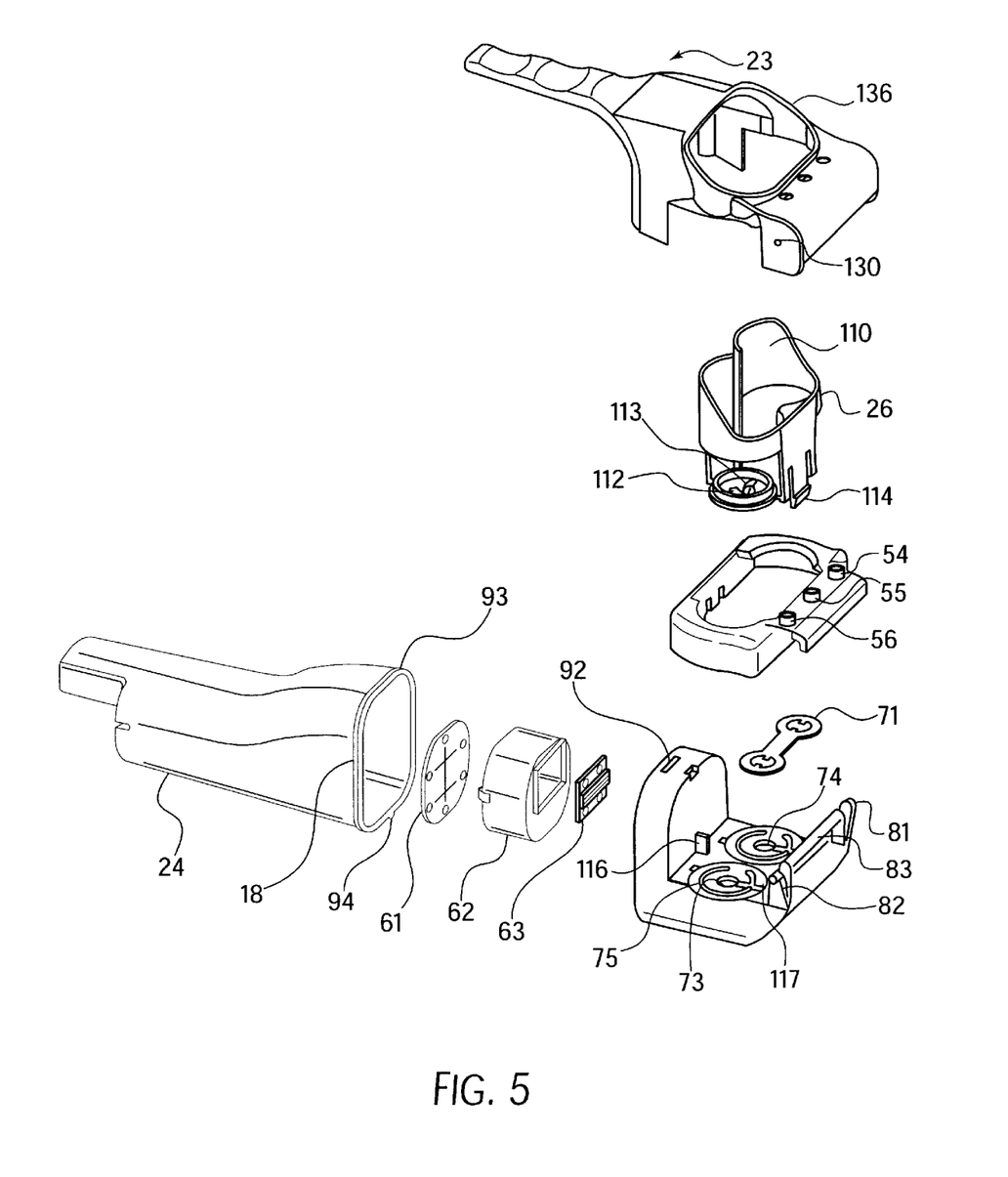
FIG. 5 shows a perspective, exploded view of one typical embodiment of the invention, including the chamber, valve, valve body, whistle, housing, canister locking mechanism, sliding selector switch, cowling, and actuator lever.

One embodiment of the present invention is an inhaler for delivery of medication from either of a first canister 10 or a second canister 11 to the lungs of a patient by inhalation through the patient's mouth. The first and second canisters are not a part of the invention, but are supplied by pharmaceutical companies. This embodiment of the invention accepts nearly all of the commonly prescribed MDI canisters, which have a compression spray outlet. The inhaler comprises a cowling 26, which is a universal receptor and holder for the MDI canisters. In a typical embodiment, a dual canister inhaler has a cowling, which is further comprised of a support structure 110, a first canister receptor and a second canister receptor. Each of the first canister receptor and the second canister receptor has a flexible fitting 113 and a ring 114. The flexible fitting is supported within the ring. The ring has an inner diameter, which supports and guides the compression spray outlets of each of the MDI canisters into the flexible fitting. The flexible fitting engages the compression spray outlet 14 (See FIG. 8) of each of the two canisters, creating a seal around compression spray outlets of the MDI canisters. The support structure of the cowling 26 has the ring and flexible fitting fixed in one end, and the other end is open, allowing the patient to insert each of the two MDI canisters, with diameter about 0.94 inches or less, into the cowling. The shape of the inner walls of the support structure 110 of the cowling is the same cylindrical shape typical of MDI canisters, but the wall of the support structure is not homogeneously solid. As shown in FIG. 5, one embodiment of the cowling has solid cylindrical walls only on the upper half of the cowling. The solid wall in the upper half of the cowling helps the patient insert the MDI canister into the inhaler. The lower half has solid walls connecting to the ring only on the front and back surfaces of the cowling. This allows a sliding selector switch to engage the lip of a MDI canister to selectively engage either one or the other MDI canister that is inserted into the cowling.

In another embodiment, the support structure of the cowling could have solid walls on the left and right of the cowling, connecting to the ring, allowing a sliding selector switch to engage the lip of a MDI canister from the front and back of the cowling. It would be obvious to one skilled in the art that other combinations are possible for allowing the sliding selector switch to engage an MDI canister in the cowling, and these alternatives are included within the scope of this invention.

Figure 8:
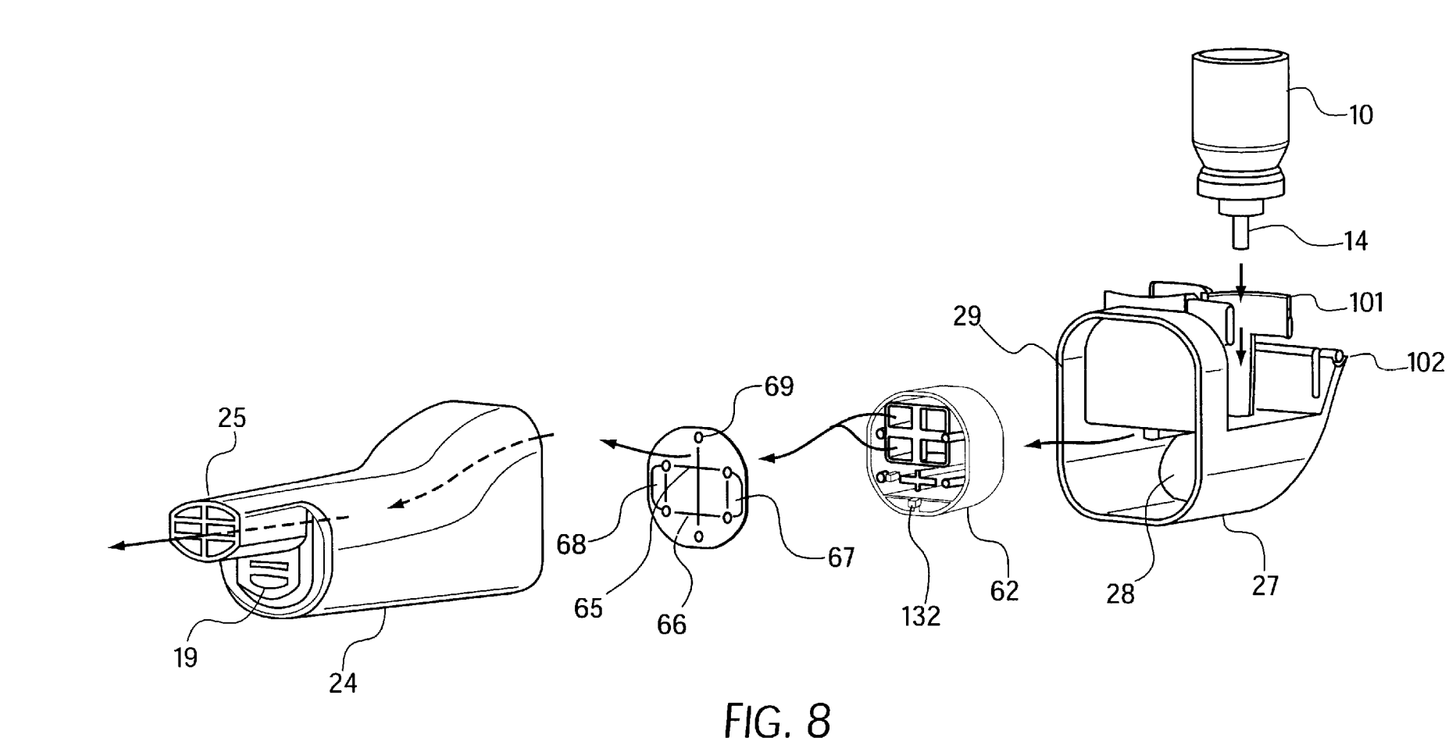
FIG. 8 shows a perspective, exploded view of a portion of one typical embodiment of the invention, including a housing, a valve body, a diaphragm valve, and the chamber body, and the path of air occurring during inhalation by the patient.

In yet another embodiment, the support structure of the cowling 101 is solid on the front and back, and their is a connecting solid between the structure supporting the two canisters, as shown in FIG. 8. In this embodiment, the exterior sides are left open. The particular embodiment shown in FIG. 8 also shows an alternative embodiment for the flexible fitting and ring. In this particular embodiment, the ring and flexible fitting were omitted intentionally, and the compression spray outlet entered directly into the cowling receiving section inlet port of the housing. A preferred embodiment of the cowling receiving section is described in detail below.

The cowling of this invention acts to hold the canisters in place, also. In an alternative embodiment, a locking plate 71 is included that mechanically locks each of the MDI canisters in place within the cowling 26. FIG. 5 shows an example of a locking plate.

Figure 6:
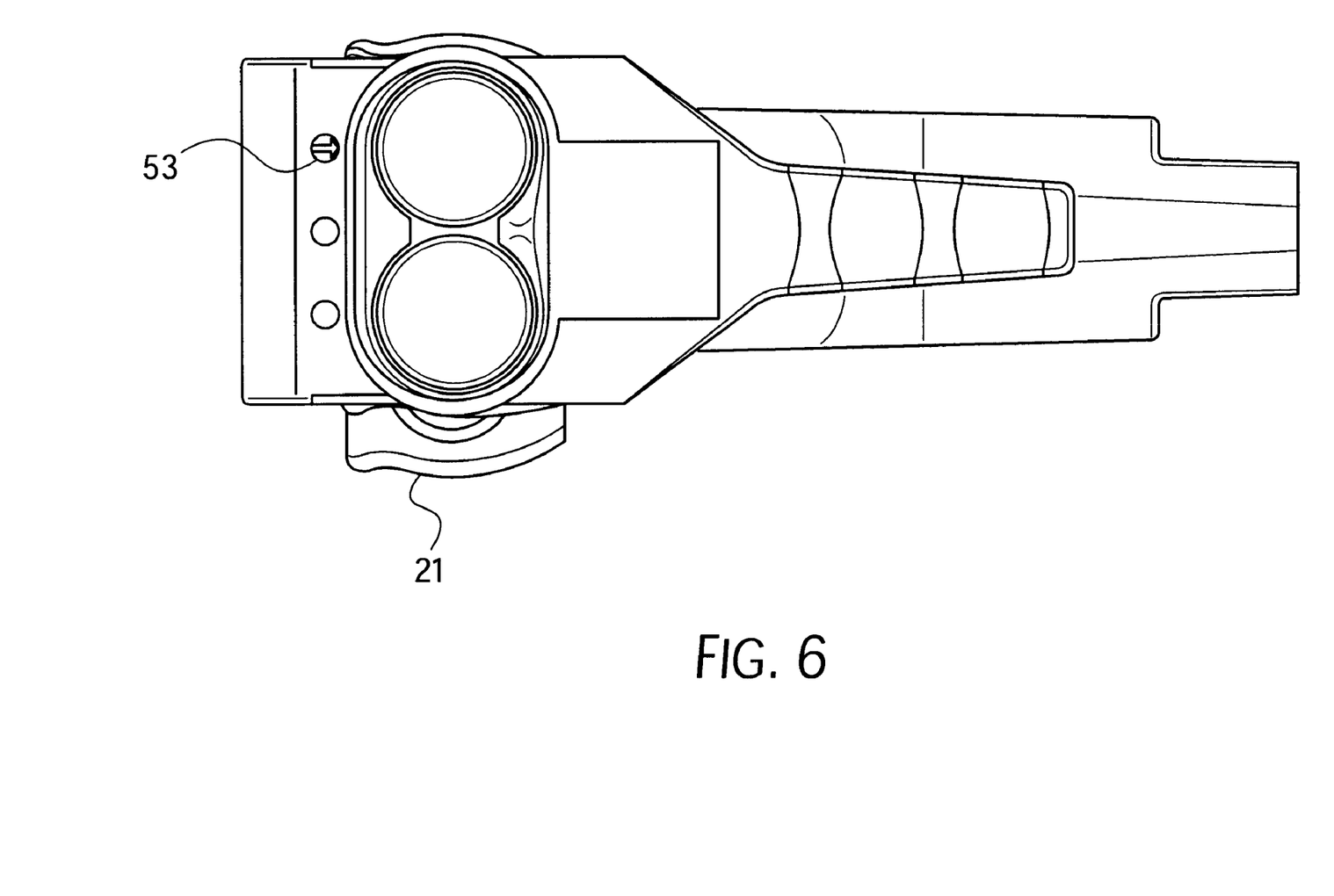
FIG. 6 shows a top view of one typical embodiment of the invention, further showing the sliding selector switch in the first position for engaging the first canister.
Figure 7:
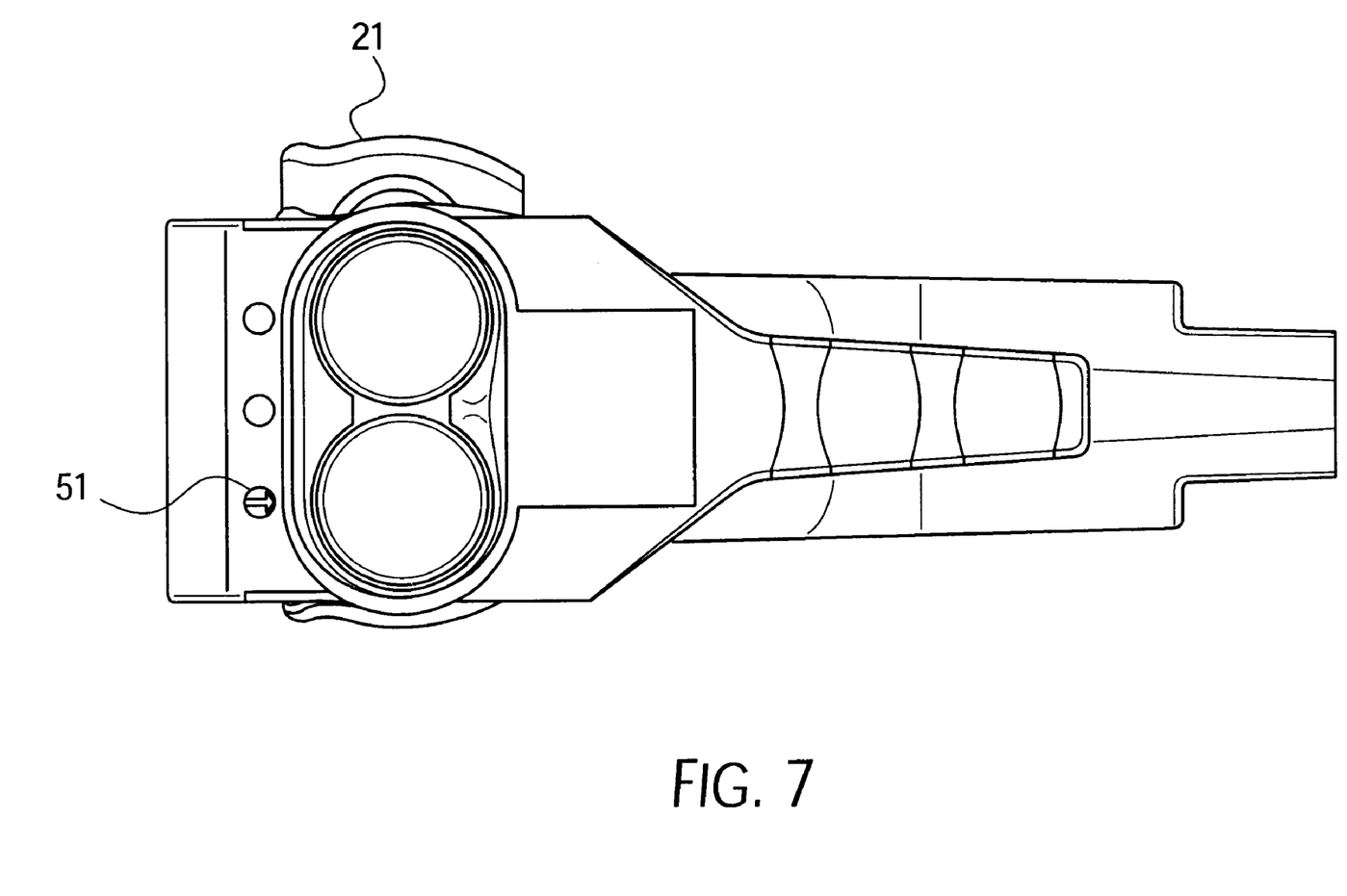
FIG. 7 shows a top view of one typical embodiment of the invention, further showing the sliding selector switch in the second position for engaging the second canister.

The previously mentioned sliding selector switch 21 has the same number of operating positions as there are canisters. Therefore, a dual canister design has both a first operating position, see FIG. 6, and a second operating position, See FIG. 7. By operating position, the inventors mean that one of the canisters is engaged by the sliding selector switch (or selector), and by depressing an actuator lever, the canister can be activated by the patient, dispensing medication. An example of an indicator display mechanism is illustrated in FIGS. 6 and 7. When the selector is in the first operating position, a first arrow 56 is visible in the first indicator window 53 and points to the first canister 10. When the selector is in the second operating position, as second arrow 54 is visible in the second indicator window 51 and points to the second canister 11.

In an alternative embodiment, the sliding selector switch 21 has a non-operative, locking position, which keeps an actuator lever 23 from being depressed by locking the actuating lever in the fully depressed position. In an alternative embodiment, the locking mechanism can lock the actuator lever in the fully deployed or up position. In yet another alternative, the locking mechanism is simply moved to a non-functional position, which engages no MDI canister; therefore, the actuator lever freely moves without engaging any canister, and this embodiment can also incorporate a means for securing the actuator lever in the fully depressed or down position. This means for securing can be a fastener, an elastic band, a twist, a hold down, a hook, a snap, a keeper mounted on the chamber body or a detent on the chamber body that engages a protrusion attached to the bottom of the lever arm that approximates the shape of a portion of an oblate spheroid. In a preferred embodiment, the lever arm would be prevented from engaging the means for securing when in an operating position, because the lever arm would never be completely depressed unless the sliding selector switch was placed in the non-operating, locking position. Then, the patient could simply snap the lever arm into the locked position.

In one embodiment the cowling 26 is a part of a larger housing assembly. Alternatively, the cowling is mechanically engaged, fastened, attached, fixed, fused or adhered within a cowling receiving section of the housing or a housing assembly of the inhaler. In general, the inventor refers to these various methods of incorporating the cowling within the cowling receiving section by the term fixedly seated; therefore, the cowling is fixedly seated within the cowling receiving section.

In one embodiment of the invention, the housing comprises a chamber receiving section 29, a cowling receiving section, a sliding selector switch support 83, a fresh air inlet 75, and an enclosed passage. In this embodiment the cowling receiving section is shaped to accept the shape of the outer dimensions of the cowling 26, and the sliding selector switch 21. As one example, the cowling can be fixedly seated in the cowling receiving section, as shown in FIG. 5, using an integral securing tab 114. The cowling receiving section in FIG. 5 has an upright centered tab support 116 and two upright pin supports, for example item 117, that seat the cowling 26 within the cowling receiving section. Other ways of fixedly seating the cowling in the cowling receiving section of the housing are known in the art and are within the scope of this invention, and the invention is not limited to the description in this particular example.

The cowling receiving section has cowling receiving section inlet ports, corresponding to the position and number of MDI canisters that the cowling accepts. For a dual canister inhaler, two receiving section inlet ports 73,74 are located in the housing. When the MDI canisters are inserted into the cowling by the patient, the MDI canister compression spray outlets are inserted into the flexible fittings of the cowling. Thereby, each of the compression spray outlets extends into the cowling receiving section inlet ports of the housing and into the enclosed passage of the housing.

The enclosed passage of the housing is defined by the inner surface of the housing (interior walls). The enclosed passage of the housing ends in the chamber receiving section. An example of the chamber receiving section 29 is the opening of the housing adjacent to the chamber, as shown in FIG. 8. In one embodiment of the invention, the interior surface of the housing defines a compression spray outlet engaging stage, also. The compression spray outlet engaging stage, in this particular embodiment, is merely a platform in the housing below the cowling receiving section inlet ports, which engages the compression spray outlets of the MDI canisters, when either of the MDI canisters is depressed by the patient, depressing the actuator lever of the inhaler. In one specific embodiment, the compression spray outlet engaging stage is defined by a protrusion of the surface of the housing back into the cavity of the housing. By protrusion, the inventors mean that the solid wall that defines the surface of the housing has an indentation on one end that extends back into the cavity of the housing, making a shelf within the housing that leaves sufficient space for the compression spray outlet to rest on the shelf, when the canister is fully inserted into the cowling. In one embodiment, the shelf gradually slopes downward toward the chamber receiving section; therefore, when the compression spray outlet of the canister is depressed, there is a gap between the shelf and the compression spray outlet. This causes the dispersal of the medication to occur in the general direction of the chamber receiving section. In another embodiment, the shelf is essentially flat, and the spray from the compression spray outlet is randomly dispersed throughout the enclosed passage of the housing. In yet another embodiment of the invention, channels are formed in the compression spray outlet engaging stage, wherein each of the compression spray outlets of the MDI canisters fit into a closed end of one of the channels, and the other end of the channels are open, directing the spray from the compression spray outlet in a desired direction within the housing of the inhaler. For example, in one embodiment, the channel directs the spray in the direction of the chamber, and in another embodiment, the channel directs the spray in a direction opposite to the chamber, enhancing mixing of the spray with external, fresh air entering through an inhalation vent in the housing prior to the spray entering the chamber through the enclosed passage of the housing. A portion of a protrusion that forms a down-sloping compression spray outlet engaging stage of one of the embodiments of the invention is shown in FIG. 8 and is labeled as item 28.

In yet another embodiment, the protrusion is replaced by a compression spray outlet engaging stage that is defined by a step-like feature in the surface of the housing. By a step-like feature, the inventors mean that, instead of a protrusion back into the housing, the housing appears to have a tread and riser of step with a nearly 90-degree angle or more preferably an arcuate transition, which similarly defines a shelf within the housing below the cowling receiving section inlet ports. This shelf performs the same function as the shelf formed by the protrusion, and can likewise slope downward toward the chamber to direct the medications toward the chamber.

In yet other embodiments of the invention, the shelf-like feature of the previous embodiments is replaced by inserts placed between the housing and the cowling. The insert of one alternative embodiment of the invention is essentially a tube with two open ends, having one end that flares to a flange and the other end having a conical shape. The conically-shaped end of the insert is inserted into the housing through the cowling receiving port, and the flared flange end centers the insert within the cowling receiving port and secures the insert in place by fixing it between the housing and the ring in the cowling. One of the inserts is placed in each of the cowling receiving section inlet ports of the housing. When the patient inserts a canister into the cowling, the compression spray outlet of the canister is inserted into the tube of the insert. The length and diameter of the tube of the insert are selected to allow nearly all of the compression spray outlets of is commonly prescribed MDI canisters to fit within the tube, with the end of the compression spray outlet resting in the taper of the conical tip of the tube of the insert. Therefore, when the patient depresses the actuator lever 23, the compression spray outlet 14 is compressed, causing dispersal of medication into the enclosed passage of the housing. In another embodiment, the inserts are mechanically attached to the housing. In an alternative embodiment the inserts are fixed to the housing. In yet another embodiment, the structure referred to as an insert is integral to the cowling receiving section inlet ports of the housing. In yet another embodiment, two inserts are joined to each other by a tab of solid between them. Other ways to compress the compression spray outlets of a MDI canister are known in the art and are included within the scope of this invention.

All of the various ways of compressing the spray outlets of the MDI canisters are referred to herein, generally, as a compression spray outlet compression mechanism. The term compression spray outlet engaging device refers solely to an insert device, and the term compression spray outlet engaging stage refers solely to a platform within the housing, which can be an attached platform or an integral compression spray outlet engaging stage. The term integral compression spray outlet engaging stage refers solely to a compression spray outlet engaging stage that is formed by a protrusion or a step-like feature in the surface of the housing, itself.

The sliding selector switch 21 is slidably and pivotally mounted on the sliding selector switch support 83. In a dual canister inhaler, the sliding selector switch is capable of engaging either canister, individually, when positioned by the patient in one of the two corresponding operating positions.

An actuator lever 23 has a lever arm 22 and a distal end 20. The distal end 20 of the actuator lever 23 is pivotally mounted on the sliding selector switch support 83 of the housing and engages the sliding selector switch 21, when the actuator lever 23 is depressed by the patient. The distal end 20 of the actuator lever 23 has a cowling opening 136, wherein the cowling 26 and canisters 10,11 pass through the cowling opening 136. In one embodiment the actuator lever is pivotally mounted to the sliding selector switch support of the housing by a pin. A more preferred embodiment is shown in FIG. 5; the distal end 20 of the actuator lever has a hole on each side 130 that engage two corresponding keepers 81,82 extending from the sliding selector switch support 83 of the housing. Yet another embodiment of the actuator lever pivotal attachment is shown in FIG. 8, which is a mechanism similar to the mechanism in FIG. 5, except that the keeper 102 is integral with the sliding selector switch support, having projecting pins from each end of the sliding selector switch support. Other methods of pivotally attaching the actuator are know in the art and are included within the scope of the invention, and the invention is not to be limited to the examples and description herein.

A chamber further comprises a chamber body, 24 a mouthpiece 25 and an housing mating section 18, wherein the chamber body is a solid shell that connects the mouthpiece at one end of the chamber body to the housing mating section at the opposing end of the chamber body. The housing mating section is an opening in the chamber, and the housing mating section 18 engages the chamber receiving section 29 of the housing 27. In one embodiment, shown in FIG. 5, the open housing mating section 18 fits into the chamber receiving section 29 of the housing 27, a tab on the top of the housing mating section 93 fits a slot in the top of the chamber receiving section 92, and another tab on the bottom of the housing mating section 94 slidably locks into a corresponding slot on the chamber receiving section. In another embodiment the housing mating section fits over the chamber receiving section, and the tabs and slots are reversed, tabs on the chamber receiving section and slots on the housing mating section. Any combination of opposing tabs and slots would suffice for joining the two sections, whether on the tops or sides of the two sections.

By using the term engages, the inventors specifically include known methods of fastening, fusing, adhering and attaching the sections to each other, but do not limit the scope of the invention thereto. Yet other means of mechanically engaging the two sections are known in the art and are included within the scope of the invention.

The mouthpiece 25 is shaped to fit the patient's mouth and has a mouthpiece vent, which allows the mixture of air and medication in the chamber body to enter the patient's mouth flow to the patient's lungs, during inhalation. An example is shown in FIG. 8. In an alternative embodiment, a face mask can be attached to end of the mouthpiece. Face masks are known in the art and are designed to conform to the patient's face for patients that cannot use the mouthpiece properly. Then inventors use the term mouthpiece to refer to the portion of the chamber that includes the surface structure of the mouthpiece, the mouthpiece vent and, in alternative embodiments of the invention, the exhalation vent or exhalation port and the valve assembly fixed within the mouthpiece end of the chamber body.

Figure 1:
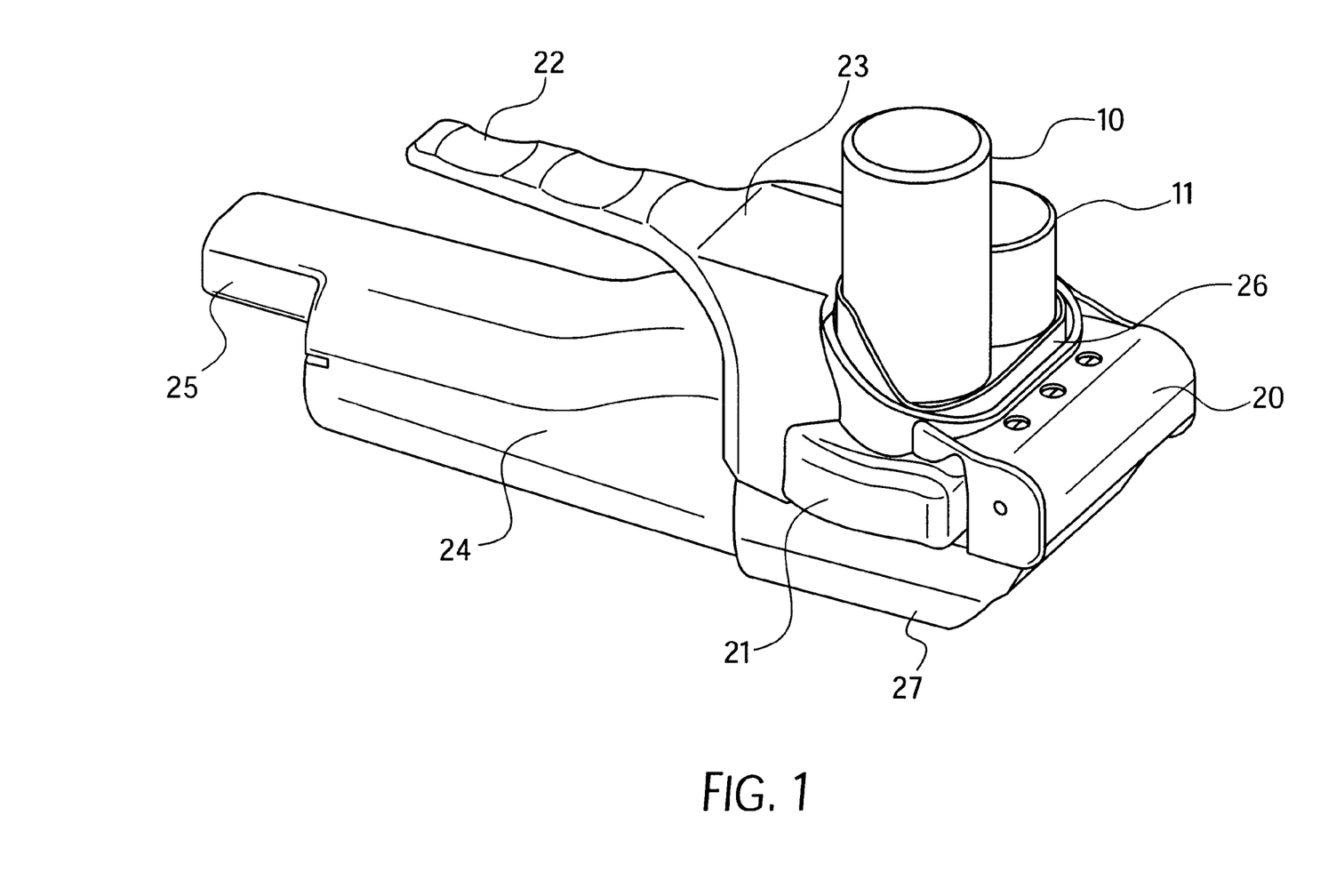
FIG. 1 is a perspective view of one typical embodiment of the invention.
Figure 2:
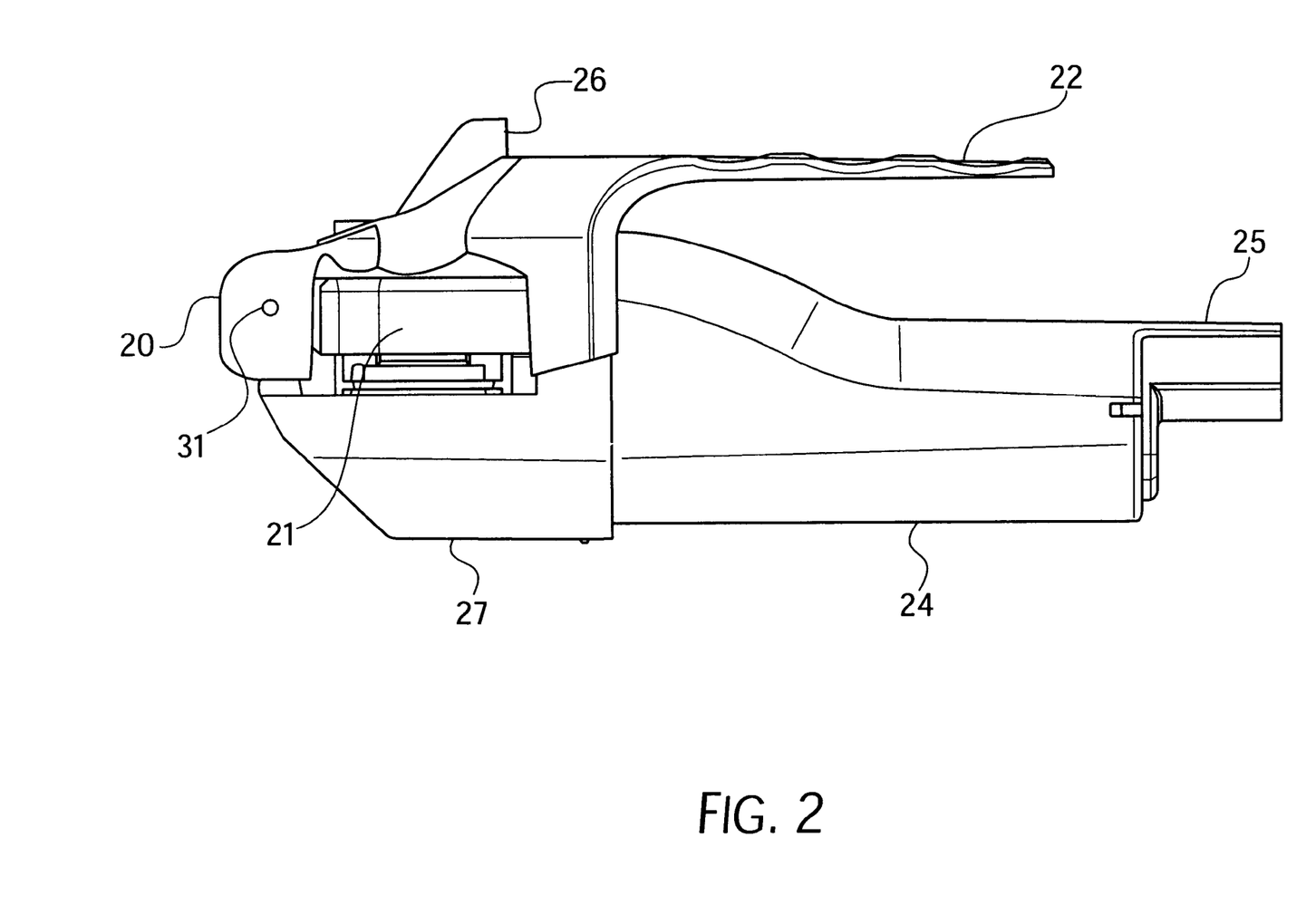
FIG. 2 is a side view of one typical embodiment of the invention, showing a pivotally attached actuator lever engaging the slidable selector switch.
Figure 3:
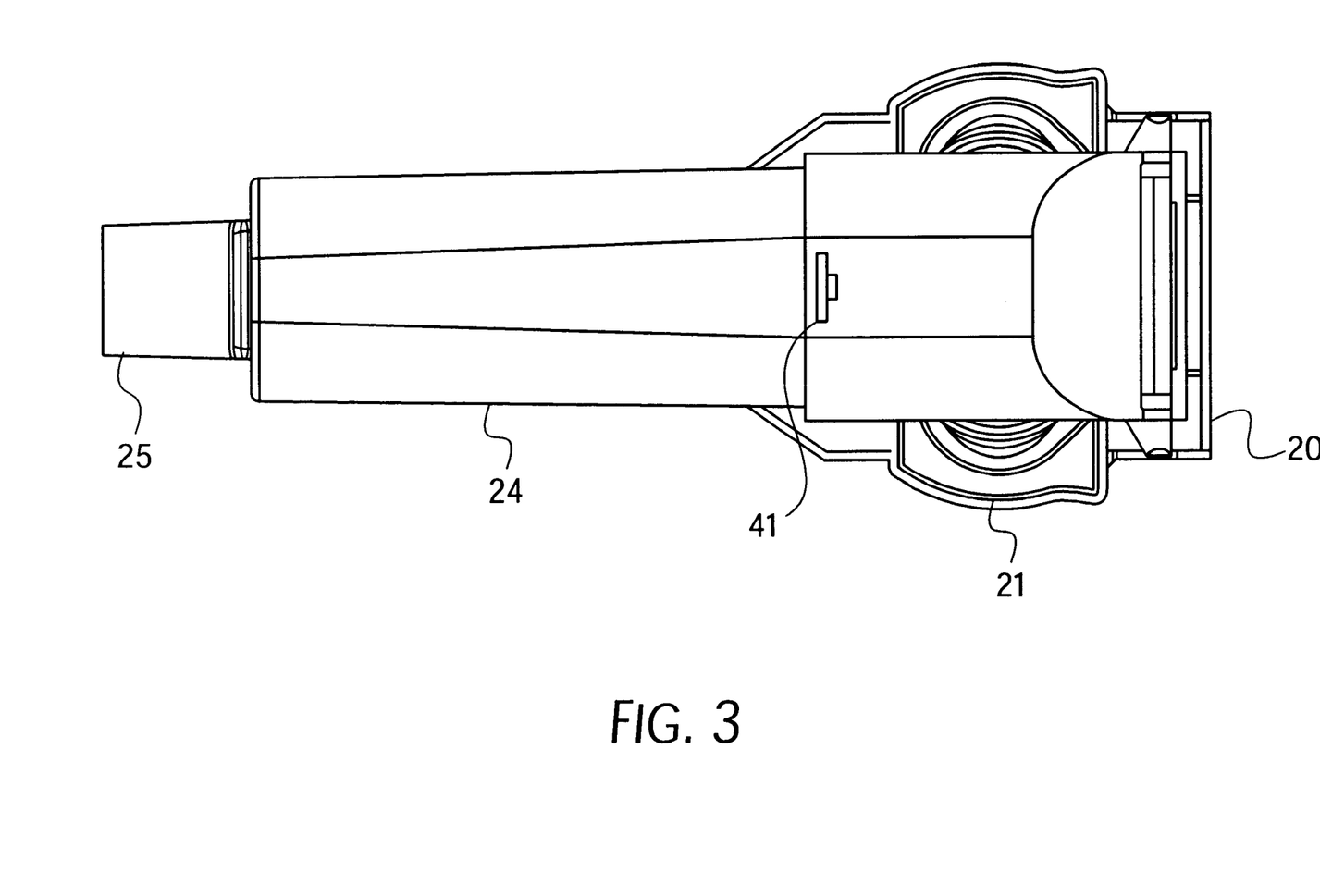
FIG. 3 shows a bottom view of one typical embodiment of the invention, further showing the mechanical attachment release tab.
Figure 4:
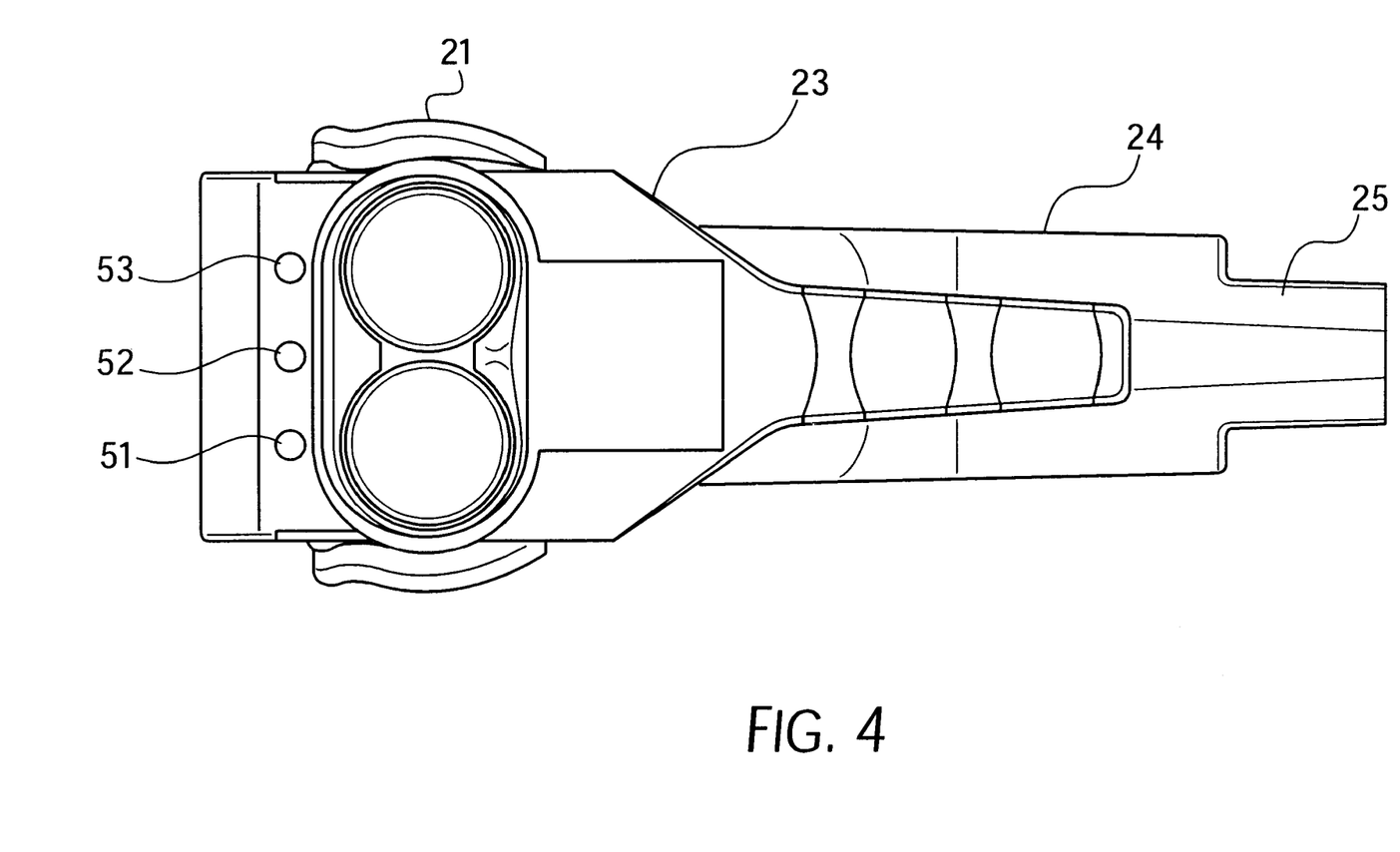
FIG. 4 shows a top view of one typical embodiment of the invention, further showing three indicator windows to indicate the operational position of the sliding selector switch.

As shown in FIG. 2, the chamber 24 opposes the actuator lever 22, and a patient can easily depress the actuator lever by squeezing the lever arm to the chamber body using the patient's entire hand, rather than only the thumb and forefinger. In addition, the actuator lever 24 provides a mechanical advantage, reducing the force that must be applied by the patient to activate an MDI canister. Depressing the actuator lever engages the sliding selector switch 21. If the sliding selector switch 21 is in the first operating position, then the compression spray outlet of the first cannister is activated. If the sliding selector switch is in the second operating position, then the compression spray outlet of the second canister is activated. Medication is dispensed from either the first canister or the second canister, respectively.

Upon dispensing the medication, the atomized mist from the inhaler is directed through the housing 27 and into the chamber 24. During inhalation by the patient, a vent in the housing brings fresh air into the housing sweeping the remaining atomized mist from the housing into the chamber, where it mixes with the air, and is drawn through the mouthpiece and into the patient's lungs through the patient's mouth. In one preferred embodiment of the invention, a valve assembly in the mouthpiece of the chamber allows the mixture of medication and air to be drawn through the mouthpiece during inhalation, but during exhalation, the inhalation valve closes, and an exhalation valve opens, allowing the exhaled air to escape from an exhalation vent in the mouthpiece. This allows the patient to inhale the medication in multiple breaths.

Examples of the diaphragm valve 61 and valve body 62 are shown in FIGS. 5 and 8. During inhalation air passes through the top cross-slit 65, and the bottom cross-slit 66 is closed against the valve body, keeping any external air from entering the mouthpiece through the exhalation vent 19. During exhalation, the top cross-slit 65 closes against the valve body, and the bottom cross-slit 66 opens, allowing exhaled air to exit through the two oval openings 67,68 on the diaphragm valve. The direction of the air reverses direction within the valve body 62, and exits through the open bottom cross-slit 65 out the exhalation vent 19 of the mouthpiece. In an embodiment without a valve assembly of any kind, there would also be no exhalation vent in the mouthpiece. The mouthpiece can be integral to the chamber, or the mouthpiece can be mechanically attached, fastened, fused or adhesively bonded to the chamber body. In a preferred embodiment, a single diaphragm valve and valve body are fixed in the mouthpiece, and the diaphragm valve is held in position by the rod-like projections (for example item 132 in FIG. 8) from the valve body that engage corresponding holes in projections extending from the mouthpiece and exhalation vent (not shown). The rod-like projections extend through the holes in the periphery of the diaphragm valve (for example item 69 in FIG. 8), and the projections extending from the mouthpiece and exhalation vent force the diaphragm valve 61 to be in direct contact with the valve body 62. In another embodiment of the invention, the inhalation valve is located at the inlet of the housing, while the exhalation valve remains in the mouthpiece. In yet another embodiment of the invention, the inhaler has an inhalation valve located in the mouthpiece, or in an alternative embodiment in the housing, and no exhalation valve is present, requiring the patient to remove the inhaler from the patient's mouth while exhaling or to exhale through the patient's nose.

The return pressure exerted by the MDI canister is sufficient to return the actuator lever 23 to the up position (or deployed position), without any additional spring mechanism. If desirable for ergonomic reasons, it is known in the art how to insert a spring mechanism into the design. For example, a coil spring could be added at the distal end, where the distal end is pivotally attached to the housing, if it were desirable to add some additional resistance to the actuator lever or for any other reason. Addition of a an additional spring mechanism is within the scope of the invention.

The standard, universal cowling is designed to accept MDI canisters of nearly all commonly prescribed medications, and the cowling helps to guide the canister into the inlet port of the housing when the patient inserts a MDI canister into the inhaler. In addition, the cowling provides support to the canister when the patient depresses the actuator lever, dispensing medication into the housing of the inhaler. Specialized cowlings may be designed for unusual MDI canisters or new MDI canisters that would not fit the universal cowling. By universal, the inventors mean that the cowling is designed to accept nearly all commonly prescribed MDI canisters.

An example of an optional audible signaling device or whistle is shown in FIG. 5. The whistle shown is installed in the valve body in the mouthpiece. In an alternative embodiment, the whistle is installed in the inlet of the housing. The term whistle is used here synonymously with any type of audible signaling device that can be made to impart an audible warning when the rate of air, or alternatively the air over-pressure, exceeds a desirable limit during inhalation. The purpose of the whistle is to alert the patient that the patient is inhaling too rapidly, allowing the patient to reduce the rate of inhalation, improving the efficacy of delivery.

What is claimed is:

1. An inhaler for delivery of medication from either of a first canister or a second canister to the lungs of a patient by inhalation through the patient's mouth, each of the first and second canisters having a compression spray outlet, the inhaler comprising:

a cowling having a support structure, a first canister receptor and a second canister receptor, wherein each of the first canister receptor and the second canister receptor has a flexible fitting and a ring, wherein the flexible fitting is supported within the ring, and wherein the support structure has a first end, an opposite end, an inner surface, and an outer surface, wherein the ring is fixed in the first end of the support structure, and wherein the opposite end of the support structure is open, allowing the patient to insert the first canister and the second canister into the cowling, and wherein the shape of the inner surface of the cowling is selected to guide each of the first canister and the second canister into the flexible fitting of the first canister receptor and the second canister receptor, respectively, and to hold the first canister and the second canister in place within the cowling;

a sliding selector switch having a first operating position and a second operating position;

a housing, wherein the housing further comprises a chamber receiving section, a cowling receiving section, a sliding selector switch support, a fresh air inlet, a compression spray outlet compression mechanism, and an enclosed passage, and wherein the cowling is fixedly seated in the cowling receiving section, and wherein the cowling receiving section has a first cowling receiving section inlet port and a second cowling receiving section inlet port, and wherein, the compression spray outlets of each of the first canister and the second canister extend through the corresponding flexible fitting of the cowling, through the corresponding first cowling receiving section inlet port and second cowling receiving section inlet port, and into the enclosed passage of the housing, and wherein the enclosed passage is defined by the surfaces of the housing and ends in the chamber receiving section, wherein the chamber receiving section is an opening in the housing;

an actuator lever having a lever arm and a distal end, wherein the distal end is pivotally mounted on the sliding selector switch support of the housing, whereby the distal end engages the sliding selector switch, when the actuator lever is depressed by the patient;

a chamber further comprising a mouthpiece, a chamber body, and a housing mating section, wherein the housing mating section is an opening in the chamber body, and wherein the chamber body is a shell that joins the mouthpiece to the housing mating section, and wherein the housing mating section of the chamber engages the chamber receiving section of the housing, and wherein the mouthpiece is shaped to fit the patient's mouth and further comprises a mouthpiece vent, and wherein the chamber body opposes the actuator lever, whereby the patient can depress the actuator lever by squeezing the lever arm to the chamber body, and whereby depressing the actuator lever engages the sliding selector switch, whereby, if the sliding selector switch is in the first operating position, then sliding selector switch engages the first canister, and the compression spray outlet of the first cannister is activated, and whereby, if the sliding selector switch is in the second operating position, then the sliding selector switch engages the second canister, and the compression spray outlet of the second canister is activated, whereby medication enters into the enclosed passage of the housing and the chamber body, and whereby, when the patient inhales through the mouthpiece, fresh air enters the enclosed passage through the fresh air inlet of the housing, whereby the mixture of air and medication in the enclosed passage of the housing and the chamber body is drawn into the lungs of the patient.

2. The inhaler of claim 1, wherein the mouthpiece further comprises a valve assembly, and wherein the valve assembly is fixed in the mouthpiece, and wherein the valve assembly comprises a diaphragm valve and a valve body, wherein the diaphragm valve opens during inhalation and closes against the valve body during exhalation.

3. The inhaler of claim 1, wherein the mouthpiece further comprises a valve assembly and a exhalation vent, and wherein the valve assembly is fixed in the mouthpiece, and wherein the valve assembly comprises a valve body and a diaphragm valve, the diaphragm valve having a top slit and a bottom slit, and wherein the top slit opens during inhalation and closes against the valve body during exhalation, and wherein the bottom slit closes against the valve body during inhalation and opens during exhalation, whereby air exhaled by the patient exits through the exhalation vent.

4. The inhaler of claim 3, wherein the valve body includes a whistle, wherein the whistle emits an audible signal, when the rate of patient inhalation causes an undesirable overpressure.

5. The inhaler of claim 3, wherein the inhaler further comprises a canister locking plate sandwiched between the cowling and the housing, wherein the canister locking plate locks both of the first canister and the second canister into the cowling.

6. The inhaler of claim 3, wherein the sliding selector switch has a non-operative locking position, and wherein, when the patient selects the non-operative locking position, the sliding selector switch does not engage either of the first canister or the second canister.

7. The inhaler of claim 3, wherein the compression spray outlet engaging mechanism is an integral compression spray outlet engaging stage.

8. The inhaler of claim 3, wherein the compression spray outlet engaging mechanism is a compression spray outlet engaging device.

9. The inhaler of claim 1, wherein the inhaler further comprises a canister locking plate sandwiched between the cowling and the housing, wherein the canister locking plate locks both of the first canister and the second canister into the cowling.

10. The inhaler of claim 1, wherein the sliding selector switch has a non-operative locking position, and wherein, when the patient selects the non-operative locking position, the sliding selector switch does not engage either of the first canister or the second canister.

11. The inhaler of claim 1, wherein the compression spray outlet engaging mechanism is an integral compression spray outlet engaging stage.

12. The inhaler of claim 1, wherein the compression spray outlet engaging mechanism is a compression spray outlet engaging device.

13. An inhaler for delivery of medication from either of a first canister or a second canister to the lungs of a patient by inhalation through the patient's mouth, each of the first and second canisters having a compression spray outlet, the inhaler comprising:

a cowling having a support structure, a first canister receptor and a second canister receptor, wherein each of the first canister receptor and the second canister receptor has a flexible fitting and a ring, wherein the flexible fitting is supported within the ring, and wherein the support structure has a first end, an opposite end, an inner surface, and an outer surface, wherein the ring is fixed in the first end of the support structure, and wherein the opposite end of the support structure is open, allowing the patient to insert the first canister and the second canister into the cowling, and wherein the shape of the inner surface of the cowling is selected to guide each of the first canister and the second canister into the flexible fitting of the first canister receptor and the second canister receptor, respectively, and to hold the first canister and the second canister in place within the cowling;

a sliding selector switch having a first operating position, a second operating position, and a non-operative locking position;

a housing, wherein the housing further comprises a chamber receiving section, a cowling receiving section, a sliding selector switch support, a fresh air inlet, an integral compression spray outlet compression stage, and an enclosed passage, and wherein the cowling is fixedly seated in the cowling receiving section, and wherein the cowling receiving section has a first cowling receiving section inlet port and a second cowling receiving section inlet port, and wherein, the compression spray outlets of each of the first canister and the second canister extend through the corresponding flexible fitting of the cowling, through the corresponding first cowling receiving section inlet port and second cowling receiving section inlet port, and into the enclosed passage of the housing, and wherein the enclosed passage is defined by the surfaces of the housing and ends in the chamber receiving section, wherein the chamber receiving section is an opening in the housing;

an actuator lever having a lever arm and a distal end, wherein the distal end is pivotally mounted on the sliding selector switch support of the housing, whereby the distal end engages the sliding selector switch, when the actuator lever is depressed by the patient;

a chamber further comprising a mouthpiece, a chamber body, and a housing mating section, wherein the housing mating section is an opening in the chamber body, and wherein the chamber body is a shell that joins the mouthpiece to the housing mating section, and wherein the housing mating section of the chamber engages the chamber receiving section of the housing, and wherein the mouthpiece is shaped to fit the patient's mouth, and the mouthpiece comprises a mouthpiece vent, a valve assembly and a exhalation vent, and wherein the valve assembly is fixed in the mouthpiece, and wherein the valve assembly comprises a valve body and a diaphragm valve, the diaphragm valve having a top slit and a bottom slit, and wherein the top slit opens during inhalation and closes against the valve body during exhalation, and wherein the bottom slit closes against the valve body during inhalation and opens during exhalation, whereby air exhaled by the patient exits through the exhalation vent, and wherein the chamber body opposes the actuator lever, whereby the patient can depress the actuator lever by squeezing the lever arm to the chamber body, and whereby depressing the actuator lever engages the sliding selector switch, whereby, if the sliding selector switch is in the first operating position, then sliding selector switch engages the first canister, and the compression spray outlet of the first cannister is depressed by the integral compression outlet engaging stage, and whereby, if the sliding selector switch is in the second operating position, then the sliding selector switch engages the second canister, and the compression spray outlet of the second canister is depressed by the integral compression spray outlet engaging stage, whereby medication enters into the enclosed passage of the housing and the chamber body, and whereby, when the patient inhales through the mouthpiece, fresh air enters the enclosed passage through the fresh air inlet of the housing, whereby the mixture of air and medication in the enclosed passage of the housing and the chamber body is drawn into the lungs of the patient, and whereby, if the sliding selector switch is in the non-operative locking position, then the sliding selector switch does not engage either of the first canister or the second canister and no medication enters the enclosed passage of the housing.

14. The inhaler of claim 13, wherein the actuator lever moves freely, when the patient selects the non-operative position of the sliding selector switch, and wherein the inhaler further comprises a means for securing the actuator lever to the chamber body.

\* \* \* \* \*